United States Patent
Benelmekki Erretby et al.

(10) Patent No.: US 11,698,381 B2
(45) Date of Patent: Jul. 11, 2023

(54) OPTO-MAGNETOPHORETIC METHOD FOR THE DETECTION OF BIOLOGICAL AND CHEMICAL SUBSTANCE

(71) Applicant: SEPMAG SYSTEMS, S.L., Barcelona (ES)

(72) Inventors: Maria Benelmekki Erretby, Sant Privat d'en Bas (ES); Sergi Gassó Pons, Sant Privat d'en Bas (ES); Lluís Miquel Martínez García, Cerdanyola del Vallès (ES)

(73) Assignee: SEPMAG SYSTEMS, S.L., Barcelona (ES)

( * ) Notice: Subject to any disclaimer, the term of this patent is extended or adjusted under 35 U.S.C. 154(b) by 737 days.

(21) Appl. No.: 16/613,401

(22) PCT Filed: May 30, 2018

(86) PCT No.: PCT/ES2018/070392
§ 371 (c)(1),
(2) Date: Nov. 13, 2019

(87) PCT Pub. No.: WO2019/229276
PCT Pub. Date: Dec. 5, 2019

(65) Prior Publication Data
US 2021/0333296 A1    Oct. 28, 2021

(51) Int. Cl.
*G01N 21/59* (2006.01)
*B03C 1/32* (2006.01)
*B03C 1/30* (2006.01)
*B82Y 5/00* (2011.01)
*G01N 35/00* (2006.01)
*B03C 1/033* (2006.01)
*B82Y 25/00* (2011.01)
*B82Y 35/00* (2011.01)

(52) U.S. Cl.
CPC ....... *G01N 35/0098* (2013.01); *B03C 1/0332* (2013.01); *B03C 1/30* (2013.01); *B03C 1/32* (2013.01); *G01N 21/59* (2013.01); *B03C 2201/18* (2013.01); *B03C 2201/22* (2013.01); *B03C 2201/26* (2013.01); *B82Y 5/00* (2013.01); *B82Y 25/00* (2013.01); *B82Y 35/00* (2013.01)

(58) Field of Classification Search
CPC ...... G01N 21/59; G01N 35/0098; B03C 1/30; B03C 1/32; B03C 1/0332; B82Y 5/00
See application file for complete search history.

(56) References Cited

FOREIGN PATENT DOCUMENTS

EP    0339623 A1    11/1989

OTHER PUBLICATIONS

G. De Las Cuevas et al., Low-Gradient Magnetophoresis Through Field-Induced Reversible Aggregation, 112 J. Phys. Chem. C 945-950 (2008).*
H. Zhou et al., Rapid Detection of DNA by Magnetophoretic Assay, 198 Sens. Actuators B 77-81 (2014).*
Z. Zhao et al., Visual Detection of Nucleic Acids Based on Mie Scattering and the Magnetophoretic Effect, 140 Analyst 7876-7885 (2015).*
K. Witte et al., Particle Size- and Concentration-Dependent Separation of Magnetic Nanoparticles, 427 J. Magn. Magn. Mater. 320-324 (2017).*
Zhao et al. "Visual detection of nucleic acids based on Mie scattering and the magnetophoretic effect" The Analyst, vol. 140, No. 23, Jan. 1, 2015, pp. 7876-7885.
J.S. Andreu et al. "Simple analytical model for the magnetophoretic separation of superparamagnetic dispersions in a uniform magnetic gradient" Physical Review E, vol. 84, 2011, p. 021402.

* cited by examiner

*Primary Examiner* — Randy Boyer
(74) *Attorney, Agent, or Firm* — Maschoff Brennan

(57) ABSTRACT

Method for detecting the presence or absence of a biological or chemical substance in a particular sample mixed with a suspension with functionalized magnetic particles, comprising: providing a light source and detector, providing a constant magnetic force perpendicular to the light's propagation direction by applying a constant magnetic field gradient, and with an absolute value which is higher than 0.1 T and measuring the change of the magnetic particle's suspension transparency versus time and comparing it with the time-variation in absence of the targeted biological or chemical substance. The method of the invention allows monitoring the transparency irrespective of the emitted wavelength and particle's optical properties.

12 Claims, 9 Drawing Sheets

OPTO-MAGNETOPHORETIC METHOD FOR THE DETECTION OF BIOLOGICAL AND CHEMICAL SUBSTANCE

BACKGROUND OF THE INVENTION

Field of the Invention

The present invention relates to a method for substance (organic, inorganic or biological) detection. In particular, the invention uses a novel magnetophoresis technique wherein materials in a sample are mixed with functionalized magnetic particles, such that the variation of the optical properties versus time are monitored and compared with the time-variation in absence of the targeted biological or chemical substance.

Description of the Related Art

Recent years have witnessed an increase in the use of clinical diagnostic methods involving immunological procedures because they are specific and have high sensitivity. Of the many heterogeneous and homogeneous immunological assay methods available, the homogeneous assays based on the agglutination of latex particles continue to be widely used in biology and medicine for the detection of small quantities of an antibody or antigen in a fluid test sample. Some advantages of these assays are that the procedures are simple, widely applicable, nonhazardous, and test results are obtained in a very short time. The agglutination reaction involves in vitro aggregation of microscopic carrier particles (usually of polymeric nature, referred to as latex). This aggregation is mediated by the specific reaction between two molecules, such us antibodies and antigens, one of which is immobilized on the surface of the latex particles to enhance the sensitivity and extend the point of equivalence. A fluid containing the ligand of interest is introduced into a suspension of the sensitized carrier particles, and the agglutination is noted as indicative of the ligand. The agglutination reaction may be used in several different modes to detect the ligand of interest, and each has its own limitations and applications. There are a number of techniques based on light scattering phenomena to detect latex particles' agglutination: turbidimetry, nephelometry, angular anisotropy, and photon correlation spectroscopy. Turbidimetry involves measurement of the intensity of the incident beam as it passes through the sample. The light beam may pass through a suspension or be absorbed, reflected, or scattered by the particles. As a consequence, the intensity of light decreases as it propagates through the suspension. For nonabsorbing particles the decrease in light intensity due to scattering is expressed as turbidity. This technique is rapid and easy to use. In fact turbidimetry does not require any special equipment other than a spectrophotometer, which is generally available in clinical laboratories.

There are fully automatic spectrophotometers that not only measure transmitted light automatically at a desired time but also dilute, pipette, and transfer to the cuvette the convenient volumes of reagents buffers and samples, incubate at a programmed temperature and make the necessary calculations using the selected algorithms and calibration curves. The possibility of running latex agglutination tests into these automatic analyzers allows the processing of hundreds of samples in a short time without investment in new instrumentation or personnel.

However, to optimize the turbidity change, which occurs during agglutination, it is important to select the appropriate particle size. For example, the number of antigen-antibody bridges between pairs of particles during the immuno agglutination is about 2-10. With larger particles, the shear forces across these bridges may result in disruption of agglutinates when pumped at high speed in automatic machines. Thus, particles of smaller diameter may yield more robust assays. For particles to agglutinate they must first collide so that antigen-antibody bridges can form. For molecules and small particles diffusion is fast enough to produce the initial collisions necessary for aggregate formation. If the particles are large diffusion is reduced (i.e., the agglutination kinetics) because the diffusion coefficient is inversely proportional to particle size. Small particles are desirable because of the requirement for increasing the collision frequency between particles or aggregates to enhance the rate of immunoaggregate production.

The turbidimetric detection depends strongly on the particle size and the incident light wavelength. It is important to select carefully the suitable particles (size) for a suitable wavelength, since the turbidity reaches a maximum with time. This maximum occurs when the signal change exceeds the optical limits of the measuring system. It has been observed by photon correlation spectroscopy that changes in aggregates size continue beyond the plateau observed in turbidimetric assays. The optimal performance may be a function of the ratio of the particle diameter to the incident wavelength, and the refractive index of particle. Thus, the selection of particle material, particle size, and wavelength of detection of the agglutination reaction are all important factors in optimizing assay sensitivity. For particles that are small in comparison with the wavelength of light, the scattering increases with the inverse fourth power of the wavelength. Shorter wavelengths, such as 340 nm, give larger signal differences during agglutination than longer wavelengths, such as 450 nm. On the other hand, the higher the refractive index of the particles at the wavelength of choice, the higher the light scattering signal.

In general, the refractive index of a material is greater at shorter wavelengths. Particles with a polyvinylnaphthalene core have been proposed to enhance sensitivity of latex immunoagglutination assays. Galvin et al. claimed that for the lowest detection limits particles should be in the size range 40-70 nm, with a high refractive index but low absorbance at the wavelength of light used.

This compromise between the size and refractive index of the particles (material), and the wavelength of the incident light can be decisive for the sensitivity of the test. As a consequence, more advanced detectors (e.g. high resolution multiwavelength-detectors) may be necessaries to conclude the test. Unfortunately, these detectors are more expensive and then more difficult to implement, especially in developing countries. In addition, the selection of the most suitable particles for each test may requires a high level of optical knowledge and an easy access to a large selection of particles.

Substantial progress has been made in developing technologies in the field of magnetic microspheres and magnetic nanospheres. Those magnetic nanospheres and microspheres containing superparamagnetic cores in a nonmagnetic matrix (hereafter magnetic particles) are used in numerous biological applications. They are used, for example, as carriers, which can be targeted to a particular site using an external magnetic field.

The above mentioned magnetic particles are designed to create magnetic particles with large superparamagnetic response. In fact these magnetic particles are typically made by embedding superparamagnetic nanocrystals in a nonmagnetic matrix such as polystyrene and nanoporous silica. The resulting magnetic particles retain the superparamagnetic response of their constituent superparamagnetic nanocrystals and show larger magnetization when an external magnetic field is applied. Further, neither coercivity nor remanence is observed at the working temperature. However, in addition to the intrinsic superparamagnetic behavior of the constituent nanocrystals, one must consider the interactions between the nanocrystals inside the skeleton matrix due to their proximity and surface effects due to the coating; these can lead to changes in the overall magnetic response of the colloidal particle.

Biomagnetic Separation (using the magnetic particles described above) has numerous applications in Life Science. From cell sorting to molecular diagnostics, this technology can be used with volumes ranging from a few nanoliters (lab-on-chip) to tens of liters (production of IVD-reagents). One of the problems of working with small tubes and classical magnetic separators (or simple magnets) is the lack of definition of the magnetic force. As the magnetic field and its gradient change with distance, the force on the magnetic particle in the suspension is not constant and variations in the behavior of the suspension are difficult to control.

EP0339623 discloses a laser magnetic immunoassay method and system based on antigen-antibody reactions. For this method, nano beads are needed and electromagnets are used to generate the magnetic force. The use of magnetic nanoparticles (D<<100 nm) implies that its magnetic moment is very small, thus each particle moves without interacting magnetically with its neighbors. The separation speed is then $v=(D^2/18n)*\mu_0*M(H)*\nabla(H)*\rho$, where D is the particle diameter, n the viscosity of the buffer and $\rho$ the density of the particle. This individual magnetophoretic behavior implies a slow separation speed and a strong dependence on the individual nanobeads characteristics. That implies a large variability due the inherent dispersion of size of a set of real magnetic particles. Moreover, the speed would also be dependent on the magnetic field profile. The use of electromagnets, with soft ferromagnetic pole pieces, makes very difficult to generate well controlled magnetic field variations, thus the attainable range of magnetic field gradients is limited, thus the attainable magnetic force. As the permeability of the pole pieces would also strongly depend on the local value of the field (including the inherent hysteresis of ferromagnetic materials), the magnetic flux path would change smoothly from point to point. The local value of the magnetic field on the pole pieces—and by consequence in the gap—will also vary with the applied magnetomotive force (Ampere turns) and its previous values. The value of the magnetic force over an individual magnetic nanobead would depend on the value of the applied intensity on electromagnet, but would be different if the current is increasing or decreasing, and if the pole pieces have been saturated or not (i.e. the applied electrical current have reach a value high enough to reach the maximal magnetization of the pole pieces' material). All these effects imply that for a given set of individual beads, its a large variation on the time needed for reaching the final position (or any specific point), and even for exactly the same distribution of physical characteristics (size, density, magnetic properties), reproducibility would require a precise electrical current control and detailed control on how it is applied to the electromagnet.

All those variations would, partially or totally, mask the magnetophoretical changes induced on the beads due to the immunocaptured target, Further, the use of a laser makes the optical system costly and complex, as the need to focus the laser at a single point and measure the scattered backlight requires a well-controlled optical environment. Also, the bulky electromagnets used to generate the magnetic force needed require high power consumption that generates heat that is difficult to manage.

SUMMARY OF THE INVENTION

The present invention provides a method for detecting the presence or absence of a biological or chemical substance based on a opto-magnetophoresis technique, wherein the materials are reacted with functionalized magnetic particles in the range of 10-1000 nm in the presence of a uniform magnetic field gradient. The method does not depend on the refractive index of the non-magnetic matrix of the magnetic particles, as in known turbidimetric techniques, and the device does not need a laser or electromagnets, the invention solving thus the problems discussed above. The method comprises the steps of providing a light source and detector, providing a magnetic force perpendicular to the light's propagation direction with a constant magnetic field gradient, with an absolute value which is higher than 0.1 T, and measuring the change of the magnetic particle's suspension transparency versus time. Systems for putting the invention into practice comprise a light source and detector, a magnetic force generator made of permanent magnets for generating a magnetic force perpendicular to the light's propagation direction, with a constant magnetic field gradient and with an absolute value which is higher than 0.1 T and processing means for measuring the change of the magnetic particle's suspension transparency versus time. In one embodiment, the magnetic force generator is formed by at least four permanent magnets following the Halbach progression for a quadrupole in a cylindrical support. In another embodiment the magnetic force generator is formed by two permanent magnets with opposite polarities and the light and the detector is an spectrophotometer.

BRIEF DESCRIPTION OF THE DRAWINGS

To complete the description and provide for better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

Figure 1:
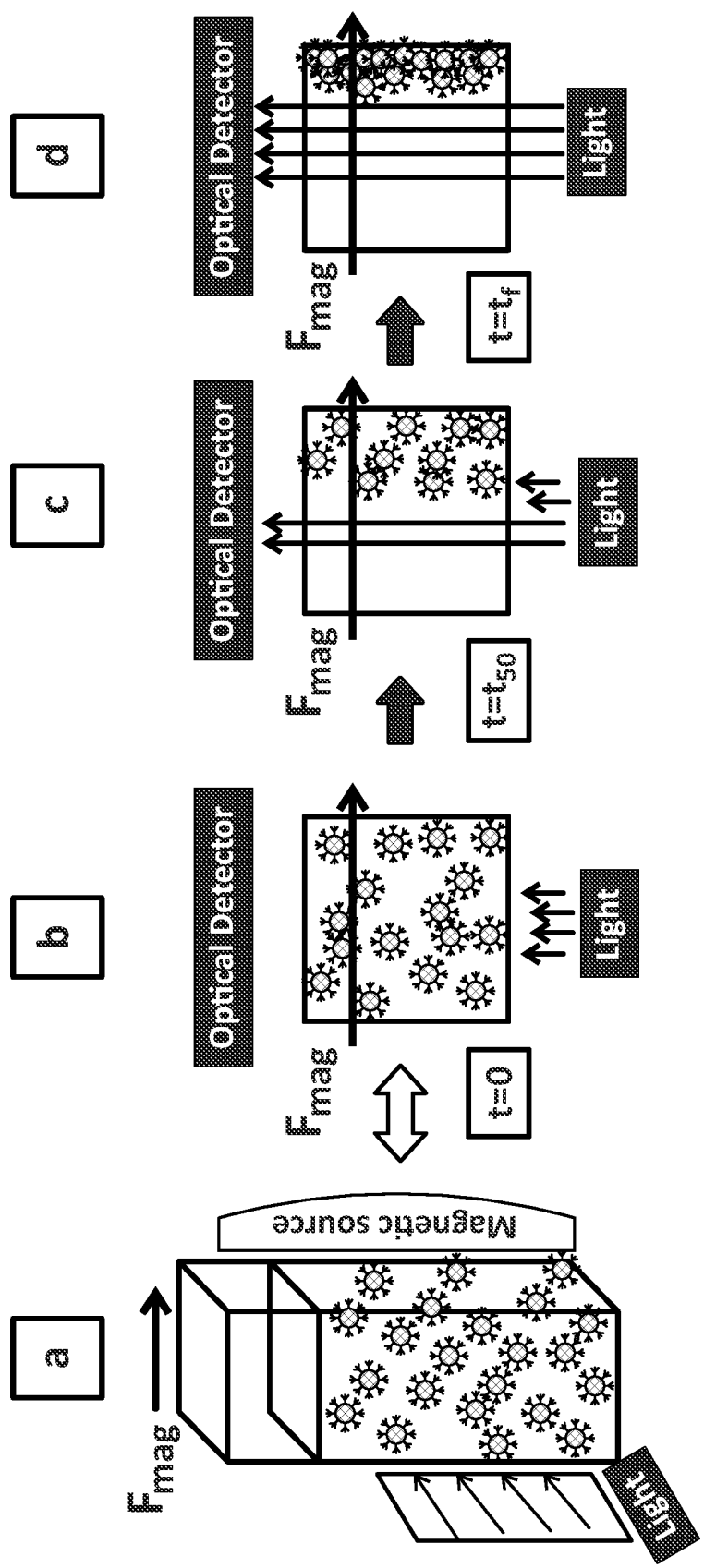
FIGS. 1a-1d show the working principle of a system according to the invention.

In the present invention, materials in a sample are reacted with magnetic particles (commercially available) that are functionalized to specifically bind to the targeted biological material in solution to produce a magnetic colloidal aggregate. The magnetic particles can be coated with protein antigens and reacted with the corresponding antibody, or with complementary or non-complementary oligonucleotides for genetic and pathogenic disease-detection. Other aggregations are based on electrostatic interaction between the magnetic particles and the biological materials, or by the absorption of the material onto the surface of the magnetic particles. In the case of microorganisms, the magnetic particles are absorbed on the surface of the microorganism. The aggregate is driven by magnetic forces towards the walls of the transparent vessel containing the suspension inducing higher transparency in the suspension. The progressive transparency of the suspension is real-time monitored. The separation speed in the present invention depends on the magnetization and size of the particles. These parameters can be adjusted by adjusting the size and the magnetic content of particles. The most suitable particles for use with the invention are particles of 200-300 nm of diameter with a magnetic content of 20-60%.

When the magnetic particles are functionalized and mixed with the analyte, colloidal aggregates containing the magnetic particles and the analyte are formed. Those aggregates, when brought under a uniform magnetic field gradient, move at a higher velocity than the initial monodispersed magnetic particles (colloids without analyte). As described by Andreu et al (J. S. Andreu et al, PHYSICAL REVIEW E 84, 021402 (2011)), the movement of magnetic particles is a cooperative phenomenon where the individual particle has enough magnetic moment for having a magnetic dipole-dipole interaction with its neighbours, strong enough to overcome thermal agitation.

If that happens, the magnetic particles form chains moving much faster than isolated magnetic particles. The average number of particles forming a chain can be estimated from the formula $N=\sqrt{(\phi_0 * e^{(\Gamma-1)})}$, where $\phi_0$ is the concentration of particles and $\Gamma$ is the ratio between magnetic and thermal energy $\Gamma=(\mu_0 \pi D^3 M_s^2)/(72 k_B T)$, where D is the particle diameter and $M_s$ its saturation magnetisation. When N>1 the magnetic particles interact and move much faster than when N<<1 and each particle moves isolated. Thus, selecting the right diameter and saturation magnetisation for the selected magnetic particle, it is possible to have it moving as an isolated particle (slow) when is not agglutinated, but moving cooperatively (fast) when its agglutinated. The particles linked through reaction with the analyte act as particles having a bigger diameter. It should be noticed that the increase in diameter has a larger effect on the value of F (even if the effective Ms would be lower for the agglutinate) and its effect over N is exponential.

This behavior induces an important difference in the magnetic separation time of the formed aggregates and the monodispersed magnetic particles. This difference in magnetic separation time is optically monitored by measuring the real time transparency of the suspension. In the case of the aggregate formation, the suspension reaches higher grades of transparency in shorter times in comparison with the suspension of the monodispersed magnetic particles. This optical monitoring (transparency of the suspension) can be performed in white light (combination of different wavelengths in the electromagnetic spectrum), or at specific wavelengths such as the UV-Visible spectrum (350 nm, 580 nm). Optical monitoring at a specific wavelength has an additional advantage over the optical monitoring using white light, as it allows the detection of aggregates at concentrations as low as 0.001%. Moreover, as the aggregates concentrate at the walls of the transparent vessel, in the region where the magnetic field is maximum, this behavior allows their collection for further analysis.

In the classical turbidimetry technique, as the aggregates remain in the suspension increasing its turbidity (lower transmittance), the particle characteristics and incident light wavelength should be carefully chosen to avoid to excess the optical limits of the measuring system. In comparison, in the present invention, it is not necessary to select particles for a suitable wavelength. As the aggregates are magnetic and are removed by the magnetic force from the suspension, the results of the experiments do not depend on the interaction of the incident light with the aggregate. In addition, many types of magnetic particles can be used (composites of iron oxide nanoparticles embedded in non-magnetic matrices).

FIGS. 1a and 1b show a lateral and top view of the magnetophoresis process according to the invention. The light propagates in a perpendicular direction to the magnetic force ($F_{mag}$) across the suspension to reach the optical detector placed at the other side of the transparent vessel. In 1c the homogeneously dispersed aggregates start moving towards the vessel wall due to the magnetic force ($F_{mag}$). At the end of the process in 1d, all the magnetic particles are close to the vessel wall and the suspension becomes transparent to the incident light. The transmitted light is detected by an optical detector indicating the end of the separation process.

To assess the time dependency of the transparency of samples with and without aggregates, a constant magnetic force is generated on the whole sample volume. For obtaining a constant magnetic force it is necessary to fulfil two conditions: a constant magnetic field gradient, and the saturation of the magnetic moment of the magnetic particles. The magnetic force must be perpendicular to the light's propagation direction.

The magnetic force acting over the magnetic particles is the gradient of the product of the magnetic moment by the applied magnetic field. If the magnetic moment of the particles is constant, the force is constant when the magnetic field gradient is also constant. At the same time, the magnetic moment of the particles depends on the applied magnetic field. When the applied field is small, the magnetic moment is proportional to the latter. The resultant magnetic moment is then the product of the volume (or mass) of the particle by the value of the magnetization of the magnetic nanoparticles embedded in the non-magnetic matrix (magnetic particles). The magnetization is the product of the magnetic susceptibility (a constant which is intrinsic to the material) multiplied by the applied field. When the magnetic field reaches a particular value, the magnetization remains almost constant, i.e. becomes saturated, and the magnetic moment of each particle is constant. The value of the applied magnetic field where the magnetic moment changes its response from linear to saturated is known as saturation field (Be).

The magnetic force generator according to the invention is a magnetic field source that generates a magnetic field with a constant gradient and absolute value higher than the saturation field in the region where the samples are placed for measuring the transparency changes. For practical purposes, a 0.1 T field is sufficient to guarantee the saturation of any commercial particles suitable for use with the invention. The speed of the magnetic particles placed at the sample holder is the result of the competition between the magnetic force and the drag force generated by the viscosity of the buffer suspension. The speed resultant of the balance of these force is proportional to the square of the magnetic bead diameter, the gradient of the applied magnetic field, the magnetization and the density of the particle, and it is inversely proportional to the buffer viscosity. For larger beads—keeping constant the other characteristics-, the separation speed is thus faster due the larger diameter. The aggregates act as larger particles and move therefore faster than the single particles For the suitable range of magnetic beads diameter and magnetic charge selected for this application (i.e. beads that moves as isolated particles when are not linked by the capture of the target, but have a cooperative magnetophoretical movement when are aggregate by the capture of the target substance), magnetic field gradients between 1 T/m and 100 T/m are needed over large volumes if the separation is to be performed in few minutes and not in several hours. These gradients (on relatively large gaps) are very difficult to obtain with electromagnets due to the limitations inherent to the use of soft ferromagnetic pole pieces. However, using modern magneto crystalline anisotropic permanent magnets, like rare-earth based materials, it is possible to add the effect of magnetic field sources with different directions without affecting the magnetisation direction of the neighbour magnets, thus generating high spatial magnetic field variations, including linear constant gradients higher than the ones attainable with larger and bulkier electromagnets and without the need of use of power supplies. Note that for very small magnetic beads as the used for Magnetic Activated Cell Sorting or the patent EP0339623, these magnetic field gradients may not be high enough to perform the separation fast enough for practical applications When the generated magnetic force is homogenous at the sample's position (i.e. the magnetic gradient is constant and the magnetic field higher than the saturation field), all the beads move at the same speed. Thus, once the farthest beads start moving, their movement marks the border between the transparent buffer and the opaque region. As all the beads move at the same speed, the optical density in the region in front of the border is constant. Under these conditions, changes in the transparency as a function of time are easy to parameterize. This leads to an easier way of correlating the presence/absence of the aggregates and accordingly, the presence of the analyte of interest.

The optical means can be as simple as a LED that generates the light, and a detector such as a photodiode or a light dependent resistor that measures the amount of light transmitted through the sample. This simple arrangement allows to place one sample with its own light source and detector to measure a single analyte, or several samples (each with its own light source and detector) inside a cylindrical cavity, allowing a multiplex or mid-plex assay that can simultaneously measure multiple analytes in a single run of the assay. It is distinguished from procedures that measure one analyte at a time.

In a first embodiment, the device has a cylindrical configuration. In this case, the required magnetic field is quadrupolar. This way, the radial magnetic field gradient is constant, with zero intensity at the cylinder axis. This also has the advantage that the obtained magnetic field profile is large enough to place several samples, where each sample has its light source and optical sensor. For this purpose, several magnets are placed in a ring-like support following the Halbach progression for a quadrupole: the magnetization direction of each magnet should be 3 times the angle respect the angular position of its center in the cylindrical coordinates systems defined by the cavity, as described in FIG. 2a.

Figure 2A:
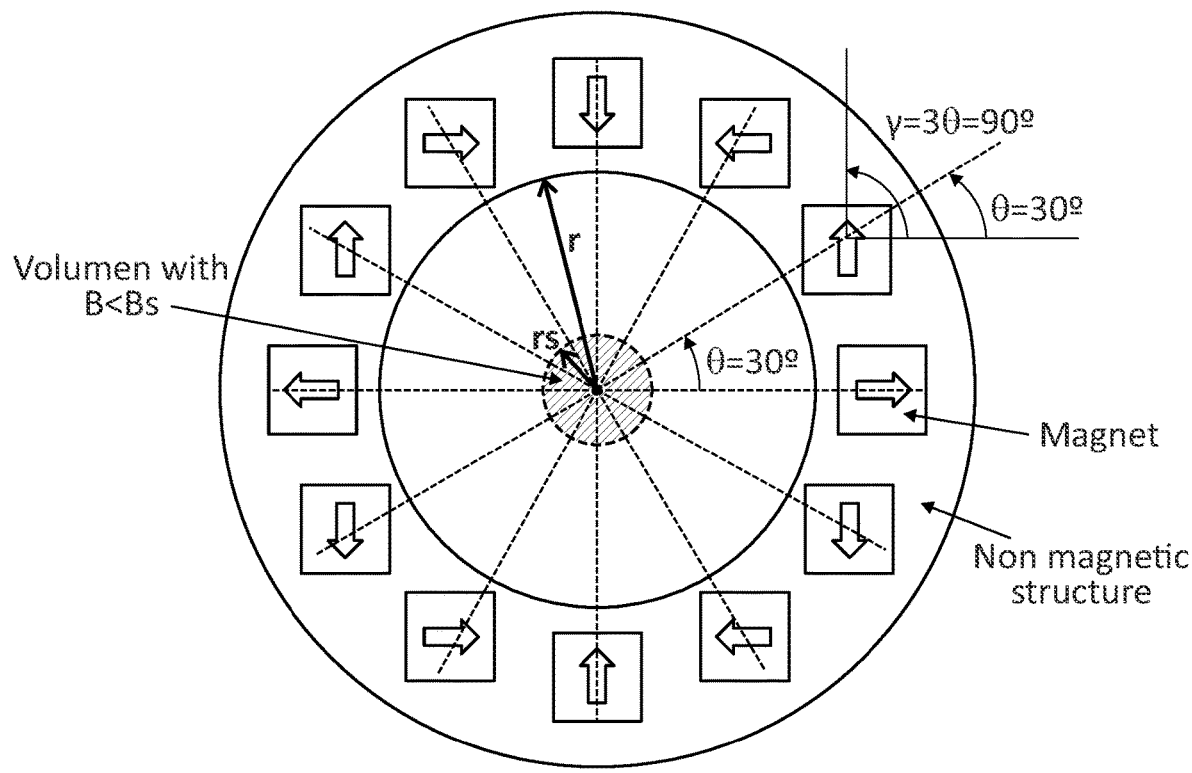
FIG. 2a is a top view of the magnetic force generator used in the invention.
Figure 2B:
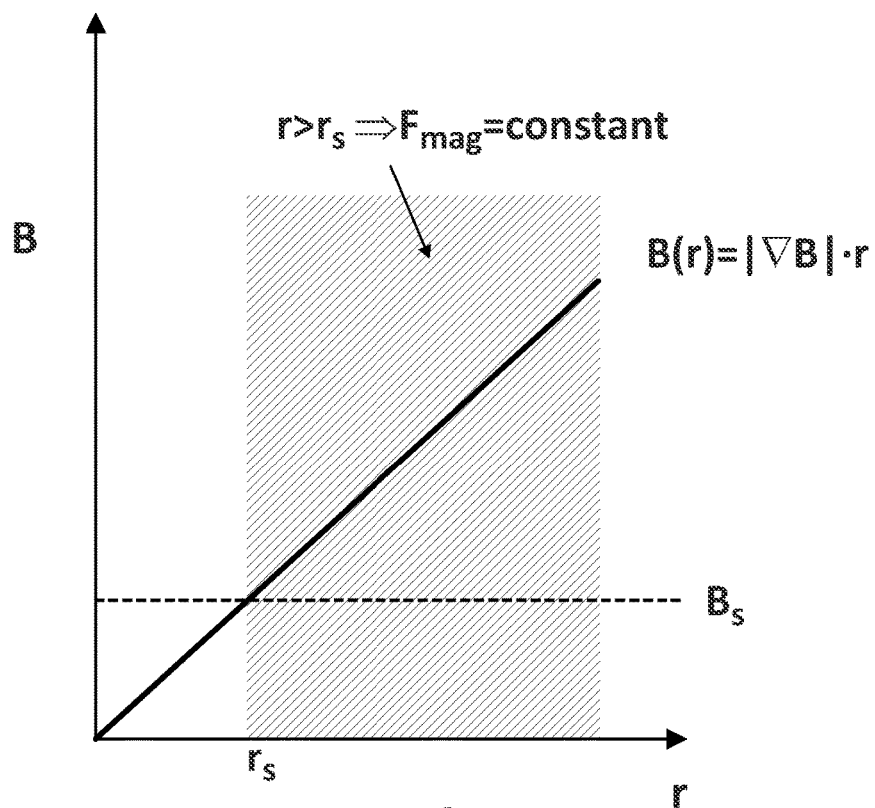
FIG. 2b is a representation of the working area described in the previous figure.

In a preferred embodiment, for a simple and easier manufacturing, square section magnets are used. N identical magnets, with N greater than 4, magnetized along one of their sides are placed at the same radial distance, R, from the center of the cylinder axis and distributed at regular angular intervals, $\theta$, where $\theta = 2\pi/N$. The permanent magnet angular position would be then $n\theta$, for $n=1, \ldots, N$, and the magnetization direction for each magnet is defined by $\gamma(n) = 3n\theta$. (FIG. 2a). If a higher magnetic field gradient is necessary, several concentric rings can be added. With this configuration, it is easy to obtain gradients in the range between 1 and 100 T/m. The samples are placed at radial distances where the magnetic field is higher than the saturation field of the magnetic nanoparticle ($B_s$). When the samples are placed at a distance $r > r_s$ ($r_s = B_s/\nabla|B|$), where $\nabla|B|$ is the value of the radial component of the constant magnetic field gradient generated by the permanent magnet assembly (FIG. 2b).

A cylindrical magnetic force generator according to an embodiment of the invention uses 12 NdFeB permanent magnets of 40 mm height and a square section of 20×20 mm magnetized along one of their sides. The magnets can be placed with their centers along a circumference of 56 mm, with an angular distance of 30° between them. As described, the magnetization should rotate 90° (30°×3) between successive magnets. This magnetic force generator would generate a magnetic gradient of 8 T/m at the central plane of the cylinder defined by the magnets. For an 8 T/m radially constant magnetic field gradient in a cylindrical cavity of 8 cm diameter, the transparent vessel containing the aggregates can be placed at a distance higher than 1.25 cm radius (0.1/8=0.0125 m) from the cylindrical axis of the cavity. As the nanoparticles move in the radial direction, the optical system is aligned perpendicular to it, i.e. tangential to the circumference defined by the sample holder center (FIGS. 3a-c).

Figure 3A:
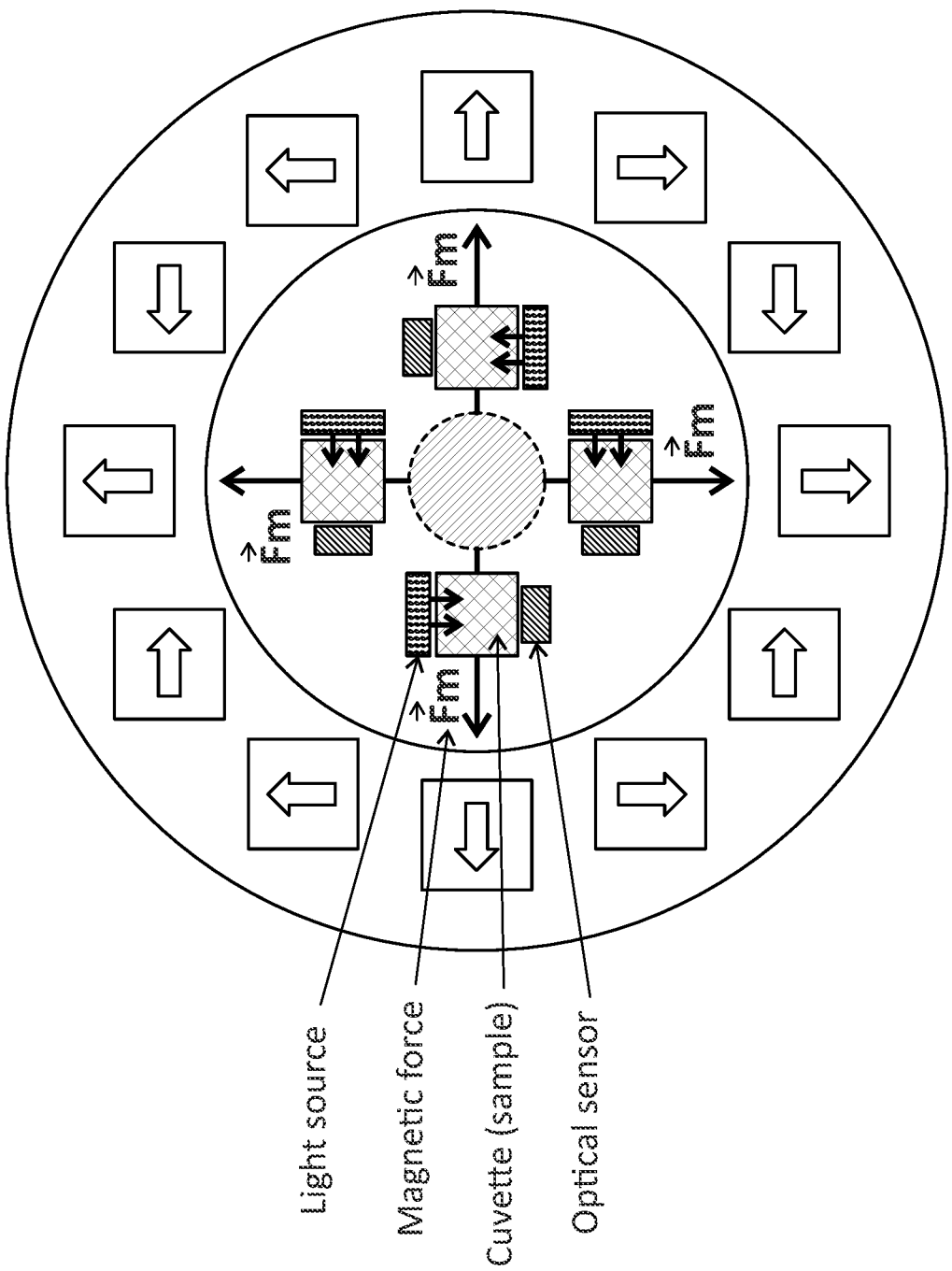
FIG. 3a shows a top view of the invention when incorporating four vessels.
Figure 3B:
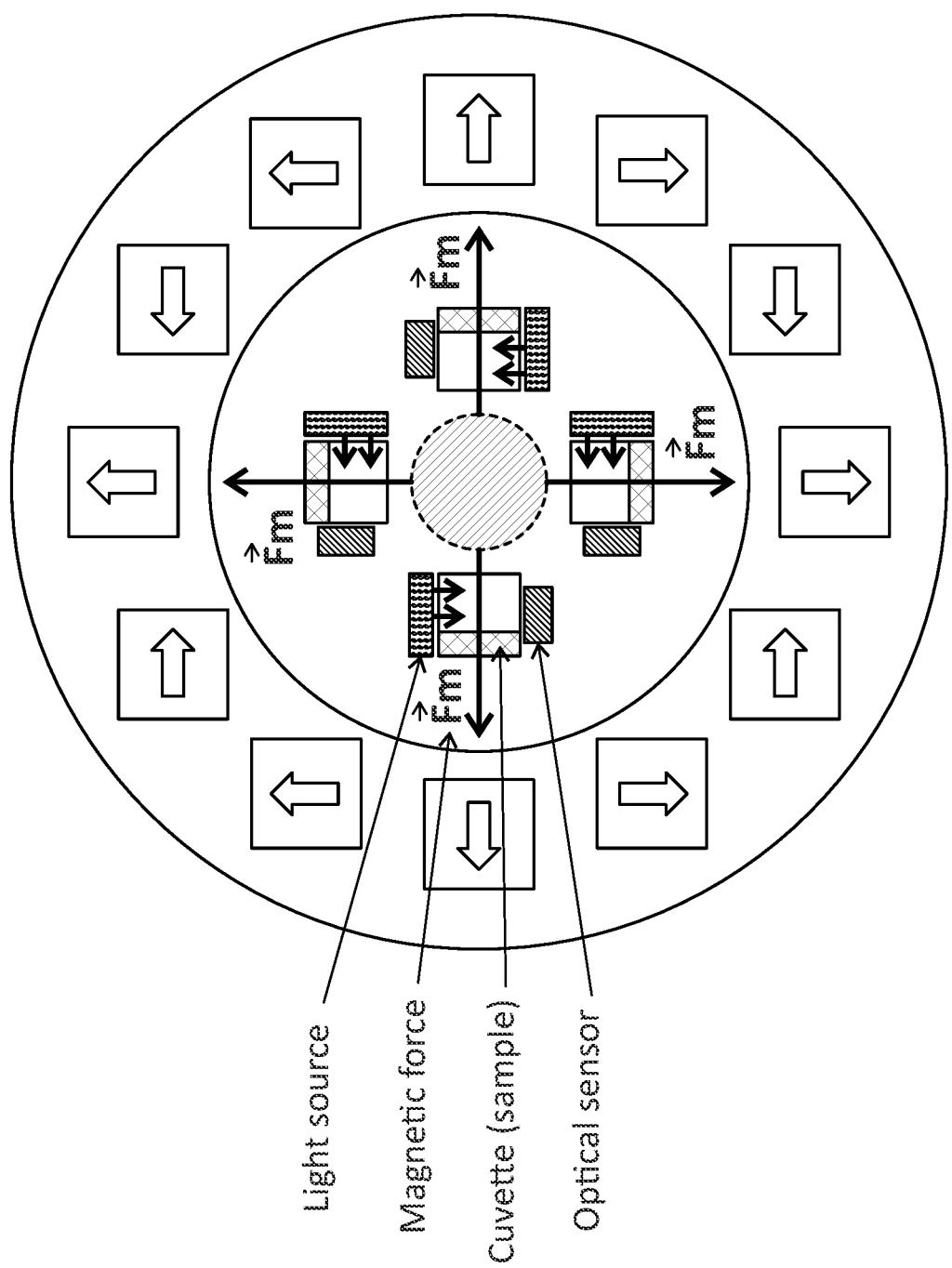
FIG. 3b shows a top view of the previous embodiment when the separation process has finished.
Figure 3C:
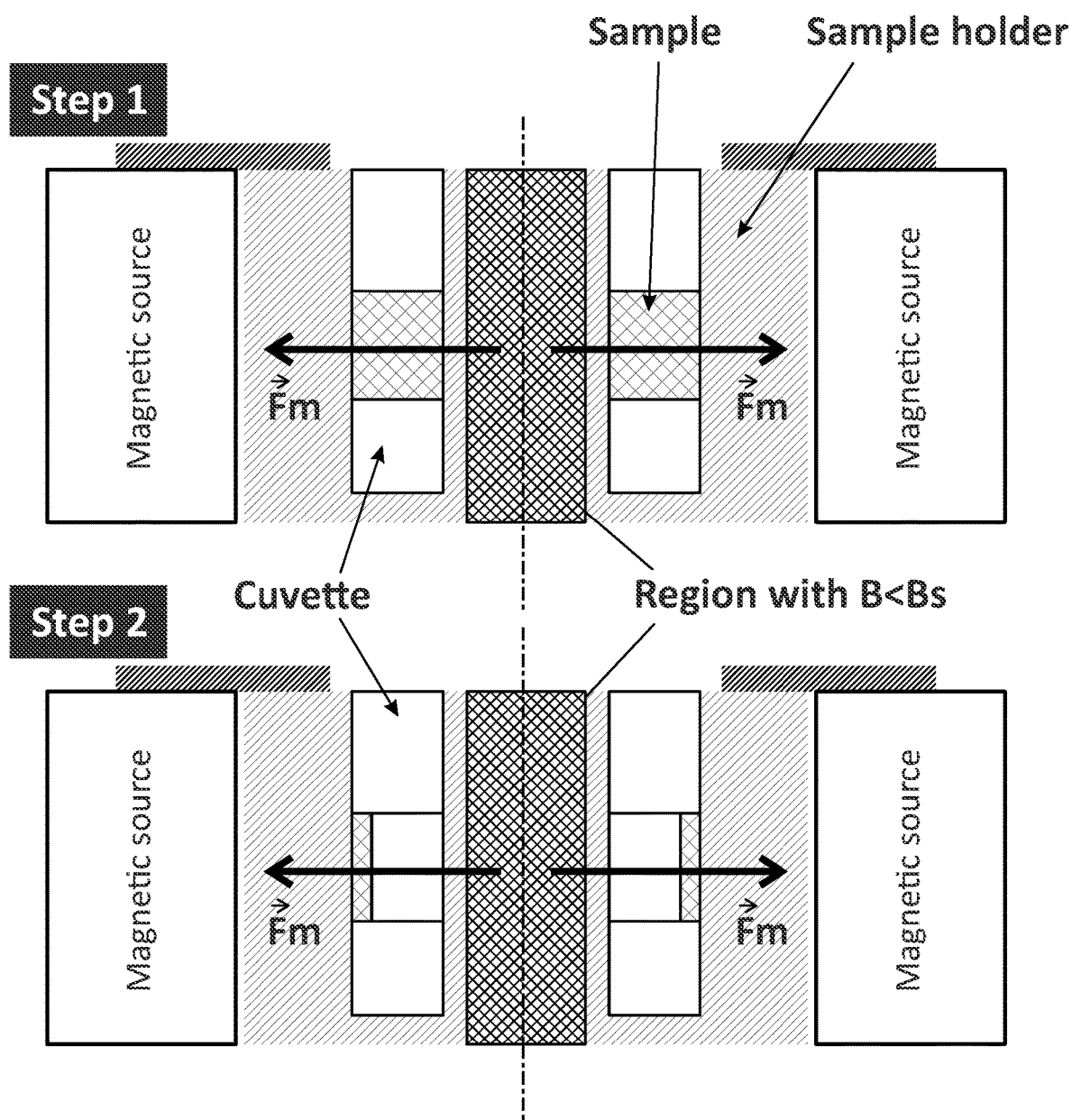
FIG. 3c shows two lateral views of the previous embodiment.

FIGS. 3a and 3b show top-view schemes of the magneto-optical device. Four cuvettes containing the samples are introduced in the device. Each sample is illuminated from one side, while the optical detector is placed on the opposite side of the transparent vessel (sample). The magnetic force is perpendicular to the direction of the light propagation. FIG. 3a represents the initial state (t=0) of the samples when they are introduced to the system. The samples are opaque to the incident light, and then no light is transmitted to the optical sensor. At the end of the separation process (t=tf), all the magnetic particles are trapped on one wall of the transparent vessel (FIG. 3b), then the suspension becomes transparent to the incident light indicating the end of the process. FIG. 3c, step 1 and step 2, show lateral-views of FIGS. 3a and 3b, respectively.

At the end of the separation process, a sigmoidal curve showing the transparency behaviour of the suspension versus the time t is obtained. The difference on the magnetic separation speed due the presence/absence of aggregates is determined measuring the time necessary to reach a certain level of transparency, for example the 50% between the minimal and maximal transparency. The time of reference is obtained using a suspension of magnetic beads without the analyte. When a new sample needs to be tested for the presence of the analyte, the same amount of magnetic beads is added, to keep concentration constant. The sample is incubated and introduced in the magnetic force generator. The change in transparency is monitored and the time necessary to achieve the defined level of transparency determined. This time can be equal to the reference time: that would indicate the absence of aggregates that would not be formed if the analyte is not present in the test sample. The second possible outcome is that the time necessary to reach the defined level of transparency is shorter than the reference time. This second result indicates the presence of aggregates—that move faster during the separation process-, formed because the analyte is present in the tested sample.

To improve the sensitivity, the experimental data can be fitted to a sigmoidal curve using the minimum squares method (or other similar algorithm). The data can then be normalized between its maximal and minimal transparency. The fitting parameters allow to get an analytical curve and determine with more precision the value of the time. For example, the experimental points (transparency vs time) can be fitted by the expression $V(t)=V_0+(V_f-V_0)/(1+(t/t_{50})^p)$ using the minimum squares method. The fitting parameters would be the $V_0$, the output of the optical sensor at the start of the process (lower value of the transparency); $V_f$, the output of the optical sensor at t=infinite (maximal transparency); $t_{50}$, the time when the sensor output is exactly the average of $V_0$ and $V_f$; and p, an exponent proportional to the slope of the curve at $t_{50}$. The transparency curve versus time can be normalized ($V_0=0\%$, $V_f=100\%$), $V_n=100\%/(1+(t/t_{50})^p)$. If the selected level of transparency is 50%, this fitting would directly provide the value of the time ($t_{50}$).

Figure 4A:
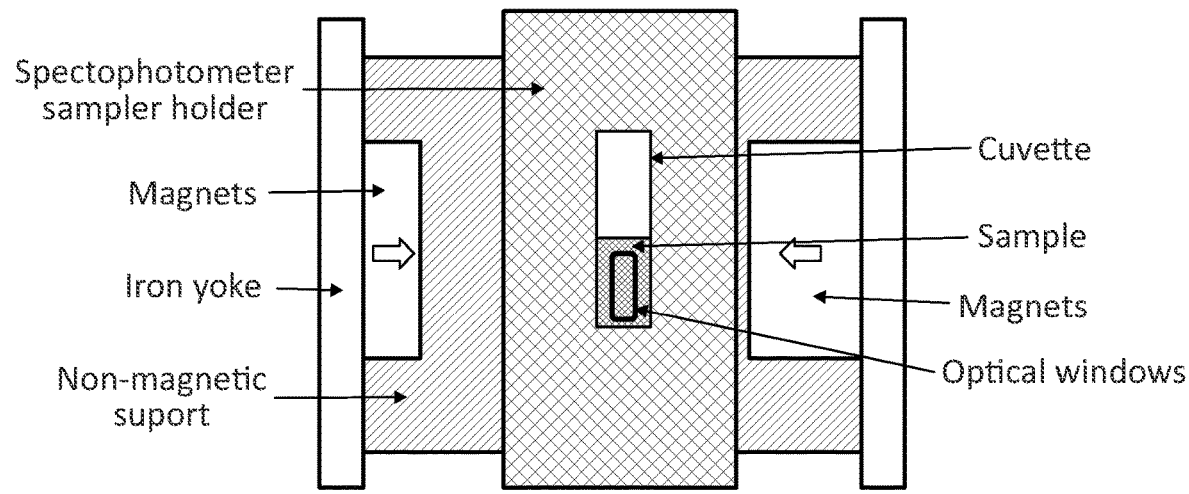
FIG. 4a shows a second embodiment of the invention with a linear configuration instead of a circular one
Figure 4B:
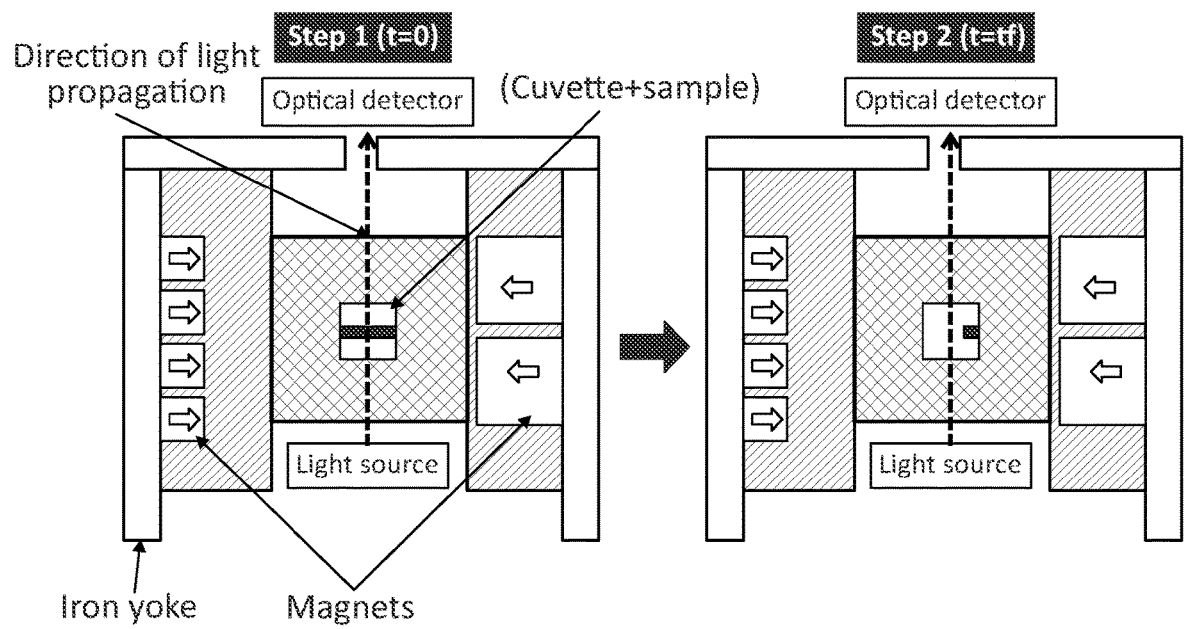
FIG. 4b is a top view of the previous embodiment.
Figure 4C:
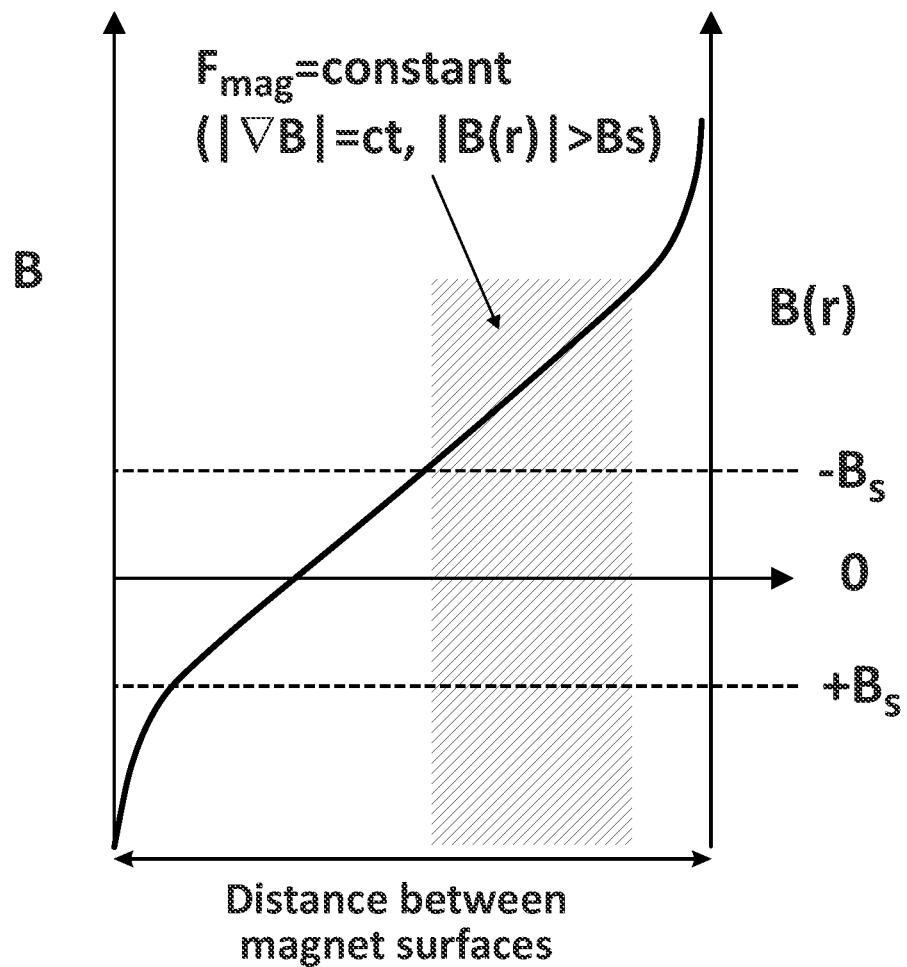
FIG. 4c is a representation of the working area described in the previous figure.

For experiments where determination of the separation time is done at specific wavelengths, a rectangular magnetic force generator is proposed, such that it can be incorporated into a spectrophotometer. Two sets of permanent magnets comprising two magnets each, is provided, which generates a homogenous magnetic force. The magnets have different thickness embedded in two parallel surfaces and with opposite polarities (FIG. 4a-4b). The light source for this embodiment is an spectrophotometer's light source (usually UV-Visible light). Light is transmitted as before in a direction perpendicular to the magnetic force direction. The assembly generates a constant gradient in the sample volume (note that the required volume is relatively small) (FIG. 4a), the same way as in the previous embodiment. By using magnets with different thicknesses and by positioning the sample closer to the thicker magnet, a constant magnetic field gradient and a magnetic field higher than the saturation field of the sample is generated as shown in FIG. 4c. This rectangular setup presents the same properties than the cylindrical setup (described in FIG. 2a in terms of the generation of n homogeneous magnetic force in the volume of the sample as shown in FIGS. 4a-ab). The design of this rectangular device allows the insertion of the sample in the working area were the magnetic field $B_r$ is higher than the saturation magnetic field $B_s$ (as shown in FIG. 4c) The use of an iron yoke (or any other soft ferromagnetic material) allows the maximization of the strength of the magnetic field gradient without increasing the size of the device, facilitating the integration within commercial spectrophotometers (as shown in FIGS. 4a-4b).

In a particular embodiment, 2 NdFeB magnets of 20×20×40 mm are placed over a 5 mm thick iron plate. Both magnets are magnetized along one of the shorter sides. The magnets are placed such that their longer sides are parallel, separated by 1 mm, aligned in its top, and with the magnetization direction pointing out of the iron plate. A second set of NdFeB magnets, with dimensions 10×10×40 mm, are placed on a second 5 mm thick iron plate. The 4 magnets are magnetized along one of the 10 mm directions, and placed parallel along the 40 mm side (separated by 1 mm) and aligned in the top. The magnetization direction points out of the iron plate. The inner face of the two iron plates (the ones with the magnets attached) should be placed parallel and with the center of the magnets aligned. With this configuration, the magnetic field gradient is constant at the central area, with a value of 7 T/m. The value of the magnetic field is zero at 20 mm from the surface of the 10×10×40 magnets, what is 15 mm from plane equidistant to the inner faces of the iron plates. As consequence, the field at the center (where the sample is placed for optical monitoring) is 0.113 Tesla, high enough to saturate the magnetic beads.

The advantage of this rectangular design over the previous embodiment is the possibility of its easy incorporation into any commercial spectrophotometers, and then the selection of specific wavelengths for measuring the transmittance variation of the suspension as a function of time while the magnetic nanoparticles are moving to the retention position. Using this combination of permanent magnet assembly and spectrophotometer optics, it is possible to distinguish samples with/without aggregates even with magnetic nanoparticle concentration below 0.001% (w/v) just comparing the time dependence of the transmittance.

In a preferred embodiment, for an immunoassay test, the magnetic particles are functionalized with an antibody or antigen, then mixed with the sample to analyse (containing the analyte). After incubation, a shorter separation time indicates the agglutination of the magnetic particles, which can be directly or indirectly proportional to the analyte content present in the sample, depending on whether the format is Immunosandwich or competitive, respectively. The system could also work without the use of antibody or antigen as a molecule capture, but with the use of aptamers (both nucleotide or peptide based), with widely used biological pairs (such as streptavidin and biotin . . . ), with molecules that present a natural capacity for binding to another molecule, and with any other alternative where there is a specific or non-specific binding between functionalized or non-functionalized particles with the analyte present in the sample. The method includes application to microorganisms and bacteria by mixing functionalized magnetic particles that recognize the microorganism in the sample to analyse. The magnetic particles can be functionalized with antibodies (or any molecule capable of recognizing and binding specifically to certain molecules exposed in the microorganism of interest). Then the microorganisms-magnetic particle aggregates are formed and monitored by the magneto-optical system. Moreover, the separated microorganism-aggregates can be collected for their incubation and subsequent analyses.

In another preferred embodiment, for oligonucleotide hybridization test, two populations of magnetic particles are each functionalized with complementary or non-complementary oligonucleotides and mixed with the sample to analyse, which might contain a complementary oligonucleotide to the one or both coated onto the magnetic particles. This sample might be the product of a PCR nucleotide amplification (DNA), the result of the DNA or RNA extraction of a particular cell or microorganism, or any other source of DNA or RNA. After incubation of the mixture, if the separation time is shorter than the separation time of the magnetic particles, this indicates the formation of agglomerates, and then the hybridization of the oligonucleotides from both particles, indicating that the sample does not contain the complementary oligonucleotide. Alternatively, the aggregation of the particles could be due to hybridization or bridging between the DNA/RNA present in the sample and the oligonucleotides conjugated to the particles.

EXAMPLES

Figure 5:
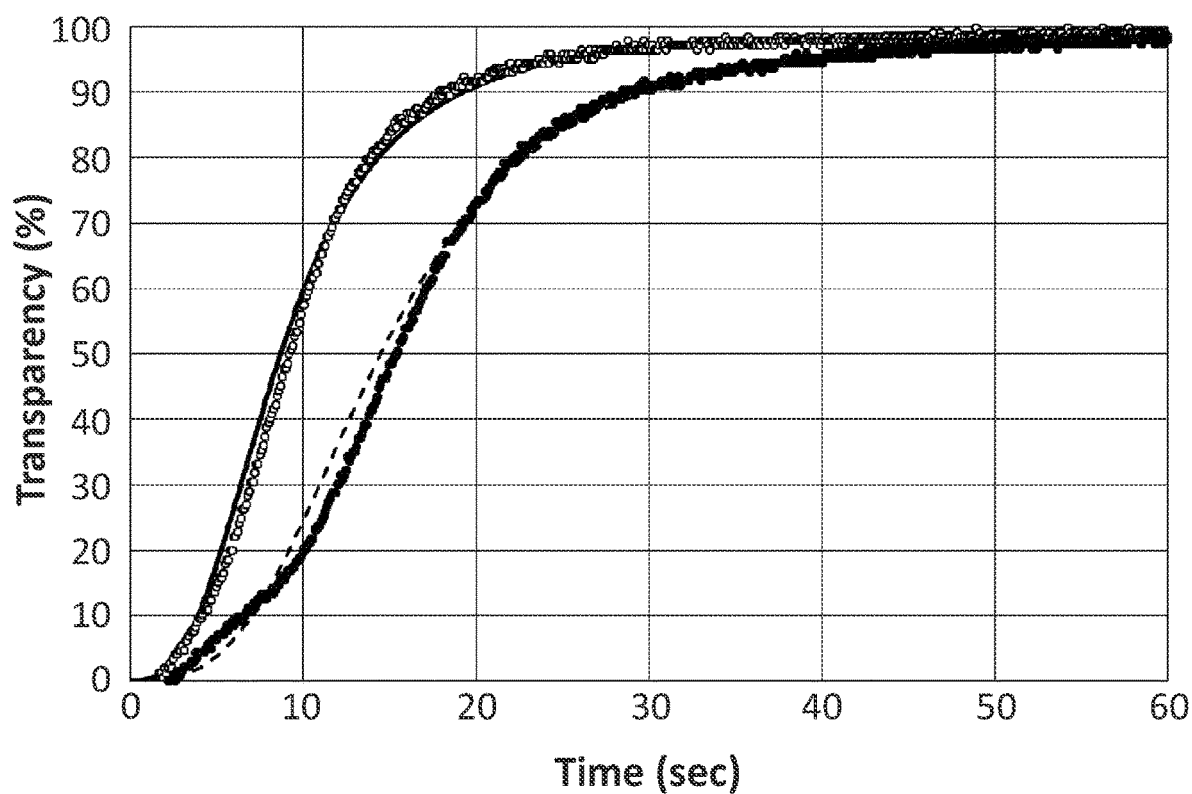
FIG. 5 shows the data of the transparency versus time during the magnetic separation for a suspension containing magnetic beads functionalized with anti-C-Reactive Protein, (CRP) antibodies.

FIG. 5 shows the data of the transparency versus time during the magnetic separation for two suspensions with a concentration of 0.1% w/v. The particles have 230 nm of diameter and 60% of magnetite content, and the separation process was done using a cylindrical magnetic force generator with a radial gradient of 14 T/m. The transparency is measured by illuminating the sample with white LEDs and placing a LDR at the opposite side. The sample, LEDs, and detector are aligned and perpendicular to the radius of the cylinder defined by the magnetic force generator. The filled symbols are the transparency versus time data obtained for a magnetic bead functionalized with anti-C-Reactive Protein, (CRP) antibodies suspension incubated with a sample without CRP. The filled symbols curve corresponds to the suspension incubated with a sample without CRP. The open symbols curve corresponds to the suspension incubated with a sample with CRP. At the beginning of the separation process (t=0), both suspensions are opaque and no light is transmitted to the optical detector. After 10-20 sec approximately, the suspensions become partially transparent and the incident light is partially transmitted to the detector and after 60 seconds both suspensions are almost completely transparent. The experimental data has been fitted, using the minimum square method to the expression, $V(t)=V_0+(V_f-V_0)/(1+(t/t_{50})^p)$, where $V_0$ and $V_f$ are the minimal and maximal transparency.

The $t_{50}$ value for the sample without the presence of CRP (filled symbol) is 14.5 seconds. The open symbol curve has a $t_{50}$ of 8.7 seconds, shorter than the reference value of 14.5 seconds, thus indicating the presence of magnetic beads aggregates due the presence of CRP in the sample. The method can be applied for detection of proteins, small molecules, microorganisms and DNA between others.

Figure 6:
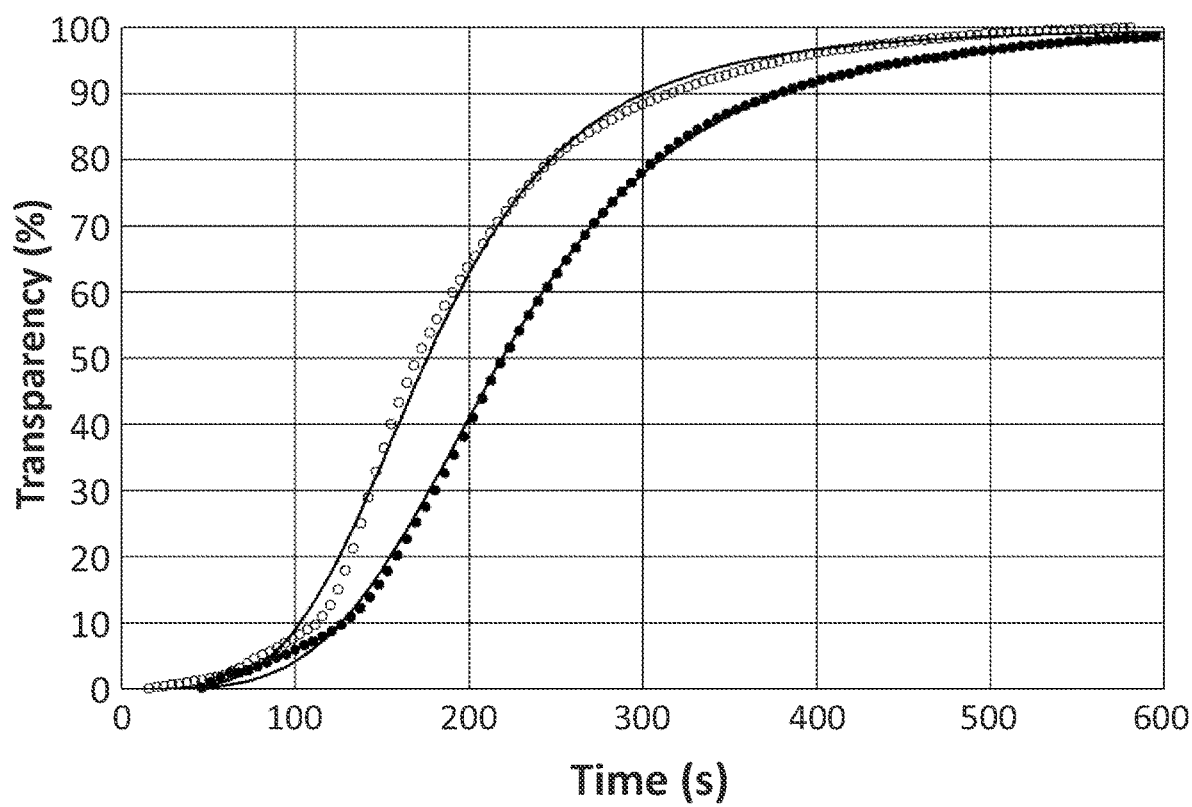
FIG. 6 shows the transparency versus time data during the magnetic separation of magnetic particles using the device described in FIGS. 4a-4b.

FIG. 6 shows the transparency versus time data during the magnetic separation of magnetic particles (240 nm of diameter and 40% of ferrite content), using the device described in FIGS. 4a-4b. The described device generates a magnetic field gradient of 7 T/m. Two suspensions of magnetic particles (0.001% w/v) were prepared and the magnetic separation process was performed in a commercial spectrophotometer at 350 nm wavelength. In one of the suspensions DNA sequence of interest is not present (filled symbols). For the second one (open symbols), the DNA sequence of interest is present. At the beginning of the separation process (t=0), the magnetic particles in the suspension absorb the incident light and then the light is partially transmitted to the detector (the spectrophotometer detector). As the magnetic particles start moving to the wall under the applied magnetic force, more light is transmitted to the detector. At the end of the process, the transmittance reaches it maximum indicating the end of the process. The experimental data have been fitted, using the minimum squares method, to the expression $V(t)=V_0+(V_f-V_0)/(1+(t/t_{50})^p)$, where $V_0$ and $V_f$ are the minimal and maximal transparency. For the sample without the target DNA sequence, the obtained $t_{50}$ is 219 seconds. For the open symbol graph, we obtain a $t_{50}$ of 176 seconds, indicating the presence of aggregates caused by the presence of the DNA sequence. Compared with the example to detect CRP (FIG. 4), the separation times are longer because of the lower concentration of the magnetic particles in the suspensions. The separation times can be shortened by using magnetic force generators with higher magnetic gradients.

As it is used herein, the term "comprises" and derivations thereof (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.) to be within the general scope of the invention as defined in the claims.

The invention claimed is:

1. A method for detecting the presence or absence of a biological or chemical substance in a particular sample mixed with a suspension with functionalized magnetic particles, the particles having a diameter between 10 and 1000 nm and a saturation magnetization such that their magnetic separation time is different in the absence or presence of the biological or chemical substance, by monitoring the optical properties of the suspension, the method comprising the steps of:
   providing a light source and detector;
   providing a constant magnetic force perpendicular to the light's propagation direction by applying a constant magnetic field gradient, and with an absolute value of the magnetic field which is higher than 0.1 T;
   measuring the change of the magnetic particle's suspension transparency versus time; and
   comparing the variation along time of the magnetic particle's suspension transparency in the presence and in the absence of the biological or chemical substance of interest,
   wherein the magnetic force is provided by a magnetic force generator comprising at least four permanent magnets following the Halbach progression for a quadrupole in a cylindrical support.

2. A method for detecting the presence or absence of a biological or chemical substance in a particular sample mixed with a suspension with functionalized magnetic particles, the particles having a diameter between 10 and 1000 nm and a saturation magnetization such that their magnetic separation time is different in the absence or presence of the biological or chemical substance, by monitoring the optical properties of the suspension, the method comprising the steps of:
   providing a light source and detector;
   providing a constant magnetic force perpendicular to the light's propagation direction by applying a constant magnetic field gradient, and with an absolute value of the magnetic field which is higher than 0.1 T;
   measuring the change of the magnetic particle's suspension transparency versus time; and
   comparing the variation along time of the magnetic particle's suspension transparency in the presence and in the absence of the biological or chemical substance of interest, wherein the magnetic force is provided by a magnetic force generator, wherein the magnetic force generator is formed by two sets of permanent magnets with opposite polarities.

3. The method according to claim 1, wherein the detector is a spectrophotometer.

4. The method according to claim 1, wherein the magnetic moment of the particles is less than $10^{-16}$ A/m$^2$.

5. The method according to claim 1, wherein the light source is a UV-visible source.

6. The method according to claim 2, wherein the detector is a spectrophotometer.

7. The method according to claim 2, wherein the magnetic moment of the particles is less than $10^{-16}$ A/m$^2$.

8. The method according to claim 3, wherein the magnetic moment of the particles is less than $10^{-16}$ A/m$^2$.

9. The method according to claim 2, wherein the light source is a UV-visible source.

10. The method according to claim 3, wherein the light source is a UV-visible source.

11. The method according to claim 4, wherein the light source is a UV-visible source.

12. The method according to claim 8, wherein the light source is a UV-visible source.

* * * * *